United States Patent
Mobassery et al.

(10) Patent No.: US 8,721,619 B1
(45) Date of Patent: May 13, 2014

(54) SAFETY DEVICE

(71) Applicant: Nellin Medical Devices LLC, La Canada, CA (US)

(72) Inventors: Hooman Mobassery, Los Angeles, CA (US); Kim Dick Man, La Canada, CA (US)

(73) Assignee: Nellin Medical Devices, LLC, La Cãnada, CA (US)

( * ) Notice: Subject to any disclaimer, the term of this patent is extended or adjusted under 35 U.S.C. 154(b) by 0 days.

(21) Appl. No.: 13/953,393

(22) Filed: Jul. 29, 2013

Related U.S. Application Data

(60) Provisional application No. 61/773,574, filed on Mar. 6, 2013.

(51) Int. Cl.
*A61M 31/00* (2006.01)

(52) U.S. Cl.
USPC ............ 604/500; 604/905; 604/284; 604/256

(58) Field of Classification Search
USPC .......................... 604/256, 500, 905, 533, 284
See application file for complete search history.

(56) References Cited

U.S. PATENT DOCUMENTS

| | | | |
|---|---|---|---|
| 5,554,135 A | 9/1996 | Menyhay | |
| 5,792,120 A | 8/1998 | Menyhay | |
| 5,951,519 A * | 9/1999 | Utterberg | 604/167.01 |
| 6,045,539 A | 4/2000 | Menyhay | |
| D607,325 S | 1/2010 | Rogers et al. | |
| 7,682,561 B2 | 3/2010 | Davis et al. | |
| 7,780,794 B2 | 8/2010 | Rogers et al. | |
| 7,922,701 B2 | 4/2011 | Buchman | |
| 7,931,877 B2 | 4/2011 | Steffens et al. | |
| 7,985,302 B2 | 7/2011 | Rogers et al. | |
| 8,231,587 B2 | 7/2012 | Solomon et al. | |
| 8,245,870 B2 * | 8/2012 | McKinney et al. | 220/375 |
| 2008/0021392 A1 * | 1/2008 | Lurvey et al. | 604/111 |
| 2012/0016318 A1 | 1/2012 | Hoang et al. | |
| 2012/0078203 A1 | 3/2012 | Gaube et al. | |

* cited by examiner

*Primary Examiner* — Kevin C Sirmons
*Assistant Examiner* — Edelmira Bosques
(74) *Attorney, Agent, or Firm* — Katherine M. Bond, Esq.; Sheldon Mak & Anderson PC

(57) ABSTRACT

The present invention provides for a safety device and methods of using a safety device for use with a medical implement having a body with an inlet end portion, the safety device comprises a bracket for mounting on the body of the medical implement; a cap supported by the bracket and sized to fit over and seal the inlet end portion of the medical implement in a safety position wherein the cap covers the medical implement; an elongate shaft having a longitudinal axis, the shaft being secured to the cap and being slidably and pivotally supported by the bracket so that the cap can be raised away from the inlet end portion of the medical implement and be pivoted about the longitudinal axis of the shaft away from the inlet end portion; and a biasing means for biasing the cap to the safety position.

9 Claims, 4 Drawing Sheets

SAFETY DEVICE

CROSS-REFERENCE TO RELATED APPLICATION

The present application claims the benefit of U.S. Provisional Patent Application No. 61/773,574, titled "Safety Device," filed Mar. 6, 2013, the contents of which are incorporated in this disclosure by reference in their entirety.

BACKGROUND

Medical practitioners routinely use needleless access systems (hubs, valves, injection ports) to remove or introduce medications or other necessary fluids, such as saline solutions or parental nutrition, into a patient. A cannula or an intravenous (IV) catheter is inserted into the patient's body creating an administration route to the patient's vascular system. However, any exposed portion of the catheter including the access port is susceptible to contamination. In the event the access port is contaminated, harmful microbes or pathogens can be introduced into the patient's bloodstream. This not only places the patient in grave danger, but also increases the complexity and cost of treating the patient.

To reduce the chance of catheter related bloodstream infections (CR-BSIs) caused by contamination, health care practitioners (hospital, outpatient, home care, hospice, or other health care settings) have implemented sanitation techniques and procedures. All practitioners wash their hands, wear gloves, and sterilize the exposed portion and surface of the access port before injecting the patient. This is commonly achieved by a medical practitioner swabbing the top portion of the port with a pad presoaked with 70% isopropyl alcohol or other disinfectant such as Chloraprep®. For many reasons this method is undesirable; therefore, there have been many attempts to create a disinfecting system or apparatus including U.S. Pat. Nos. 5,554,135; 5,792,120; 6,045,539; 7,682,561; and 7,931,877. However, all the listed attempts suffer from one or more disadvantages, including the consistency of cleaning procedure, ease of use and possible contamination from accidental impact.

Therefore, there is a need for a safety device that effectively protects and disinfects the access port that is user friendly and prevents unintended exposure thereby reducing the potential for patient infection.

SUMMARY

A safety device having features of the present invention will address these issues. The safety device is for use with a medical implement having a body with an inlet end portion, the safety device comprises a bracket for mounting on the body of the medical implement; a cap supported by the bracket and sized to fit over and seal the inlet end portion of the medical implement in a safety position wherein the cap covers the medical implement; an elongate shaft having a longitudinal axis, the shaft being secured to the cap and being slidably and pivotally supported by the bracket so that the cap can be raised away from the inlet end portion of the medical implement and be pivoted about the longitudinal axis of the shaft away from the inlet end portion; and a biasing means for biasing the cap to the safety position.

As disclosed herein, the safety device has been developed to be used with IV medication systems that administer medication or fluids through a catheter port using non-needle connections. The safety device when used with the needleless intravenous medication system ensures the access port is always disinfected regardless of the techniques used in catheter care. This device also decreases the possible incidences of access port contamination. Additionally, the device prevents microbial colonization by continuously bathing the port in an antimicrobial or antibacterial solution. The device provides a high level of protection even in the presence of heavy contamination. By keeping the access port sanitized, the chances of introducing infectious agents into a patient via a catheter access port are significantly reduced.

Alternatively, in another embodiment, the safety device further comprises a medical implement having a body where the bracket is molded as one piece with the body of the medical implement. Presently, the access ports or needles hubs do not have a "built-in" system in order to protect the exterior of the access port from pathogens. When the safety device is integral with the medical implement the cap can be replaced once the effectiveness of the disinfectant wears off. A new cap having a new presoaked disinfecting pad attached to a shaft can be inserted or secured to the device having all the same functionality as the previous cap.

In still another embodiment, the safety device further comprises a releasable lock, where the releasable lock temporarily secures the cap away from the inlet end portion of the medical implement. When the cap is rotated away, a "locking" mechanism keeps the cap displaced from the site making it easy for the practitioner to make the injection. This means the practitioner does not have to hold onto or put down the "disinfecting" tool while making an injection. Once the injection is made, the cap is rotated back toward the site, engages the "unlock" position and returns downward onto the surface of the access port into the safety position.

In another embodiment, the safety device requires two movements to dislocate the protective cap from the access port. For example, in the first movement, the cap is raised vertically away from the body and secondly the cap is rotated away from the access site. This is important because disinfecting devices that can automatically be removed from the injection site with little to no force may result in the access port being unintentionally exposed. Unfortunately, patients routinely have an access system, IV or catheter, inserted for long periods of time. Patients are required to sleep, eat, use the restroom, and move around, all with the catheter attached. An automatic or easy to remove disinfecting apparatus can be easily dislodged exposing the site to contamination without the practitioner or patient ever knowing the injection site was exposed. The exposure may even remain unnoticed until the next infusion has to be made. This problem is avoided by having a safety device that requires two movements to remove the disinfecting device from the access port.

In another embodiment, the present invention provides for a cap that has an interior space defining an area for an antimicrobial agent. In a further embodiment, the interior space comprises an antimicrobial agent such that the antimicrobial agent is configured to contact the inlet end portion of the medical implement in the safety position. In a further embodiment, the antimicrobial agent is selected from the group comprising, alcohol, isopropyl alcohol, chlorohexidine and combinations thereof. In another embodiment, the cap further comprises a rim, where the rim supports the antimicrobial agent.

The present invention protects the access port from contamination by pathogens. The safety device is secured to the body of the medical implement and the cap is placed over the exposed portion of the access port in a safety or rest position. In this position, the access port is continuously bathed in the disinfecting solution protecting the surface of the access port from viruses and bacteria. This is achieved by the interior of the cap having a pad or other material presoaked with a disinfectant. When the cap of the safety device is in the safety position, the pad is in contact with the surface of the injection site and the access port is disinfected. When the practitioner moves the cap away from the site the surface is "wiped" or "scrubbed" with the pad preparing the port for infusion.

In another embodiment, the cap further comprises a hinged door where the hinged door can be opened so that the antimicrobial agent can be removed or inserted. Whether the safety device is integral with the medical implement or removably attached with a bracket, a portion of the cap can be opened. When the cap is opened, a new sponge material soaked in disinfectant can be inserted into the cap. The cap is then closed securing the sponge inside. A rim along the bottom of the cap holds the sponge in place so when the cap is displaced from the access site the sponge does not fall out.

In another embodiment, the safety device further comprises an indicator which visually signals a change in the antimicrobial agent. The visual indicator can alert the practitioner if there is an unexpected change in the antimicrobial agent or alternatively if the antimicrobial agent needs to be changed.

In another embodiment, the present invention provides for a method of preventing contamination of a medical implement having a body with an inlet end portion, the method comprises providing a safety device for the medical implement, the safety device comprising a bracket for mounting the device on the body of the medical implement, attaching the bracket to the body of the medical implement, and covering the inlet end portion of the medical implement with a cap supported by the bracket and sized to fit over the inlet end portion of the medical implement in a safety position.

In yet another embodiment, the method further comprises the steps of removing the cap from the inlet end portion of the medical implement by slidably raising the cap away from the inlet end portion of the medical implement and pivotally rotating the cap away from the medical implement and inserting or withdrawing fluids from the inlet end portion of the medical implement.

In still another embodiment, the method further comprises the steps of after removing the cap from the inlet end portion of the medical implement by slidably raising the cap away from the inlet end portion of the medical implement and pivotally rotating the cap away from the medical implement, temporarily securing the cap away from the inlet end portion of the medical implement by engaging a lock and releasing the cap from the lock after inserting or withdrawing fluids from the inlet end portion of the medical implement.

In another embodiment, the cap has an interior space defining an area for an antimicrobial agent. The interior space can optionally comprise an antimicrobial agent such that the antimicrobial agent is configured to contact the inlet end portion of the medical implement in the safety position.

The safety device is more reliable than other disinfecting techniques because the cap is attached to the medical implement and therefore it is not subject to being misplaced, lost or contaminated. When a disinfecting device is not attached to the implement, the practitioner has to take extra steps to prepare the access port before making an infusion. For example, a disinfecting cap can be "screwed" onto the top of a needleless hub and rotated around to disinfect the port. The practitioner has to hold the port, grab the cap either from a box or strip, expose the disinfecting portion of the cap, place the cap over the port, rotate around the port and discard. In the event the cap can be reused, once the practitioner swabs the port with the cap, the practitioner either has to hold onto the cap while making the injection or put the cap down further exposing it to contamination. The practitioner can also forget to replace the sterilization cap altogether. Therefore, it is desirable to have the disinfecting device temporarily removable from the access port so that it is not exposed to contamination by being put down or possibly being misplaced. When the practitioner returns the cap to its safety position the exposed portion of the access port is once again covered, protecting the medical implement from contamination.

The safety device disinfects the access port in a consistent manner. The device is designed so that even if the practitioner is distracted or hurried the injection site is effectively cleaned. When using a wipe soaked in disinfectant or a "screw" cap, the cleaning technique is subjective as to how the port is cleaned. Additionally, the more intricate the design of the needleless catheter the more difficult it can be in reaching all surfaces to clean adequately before each use. Improper, hurried or sloppy cleaning procedures can lead to a greater chance of contamination.

It is contemplated that the safety device can be used over a period of 3 days before the disinfectant is no longer effective. In this scenario, the practitioner will have to replace the safety device on the medical implement to ensure the access port is effectively disinfected. Often times, nurses and other medical practitioners are short staffed, extremely busy and working under long arduous conditions. Therefore, safety measures that are less of a hassle and still keep the patient safe are most desirable.

DRAWINGS

The following drawings form part of the present specification and are included to further demonstrate certain aspects of the present invention. The invention may be better understood by reference to one or more of these drawings in combination with the detailed description of specific embodiments presented herein where:

DETAILED DESCRIPTION

The present invention is directed toward a safety device and methods for using the same. In the following description, numerous specific details are set forth to provide a more thorough description of embodiments of the invention. It will be apparent, however, to one skilled in the art, that the embodiments of the present invention may be practiced without these specific details. In other instances, well known features have not been described in detail so as not to obscure the invention.

DEFINITIONS

It is noted that, as used in this specification and the appended claims, the singular forms "a," "an," and "the," include plural referents unless expressly and unequivocally limited to one referent. Thus, for example, reference to "a compound" includes two or more different compounds. As used herein, the term "include" and its grammatical variants are intended to be non-limiting, such that recitation of items in a list is not to the exclusion of other like items that can be substituted or other items that can be added to the listed items.

As used in this disclosure, except where the context requires otherwise, the term "comprise" and variations of the term, such as "comprising," "comprises" and "comprised" are not intended to exclude other additives, components, integers or steps. Thus, throughout this specification, unless the context requires otherwise, the words "comprise", "comprising" and the like, are to be construed in an inclusive sense as opposed to an exclusive sense, that is to say, in the sense of "including, but not limited to."

As used in this disclosure, except where the context requires otherwise, the method steps disclosed are not intended to be limiting nor are they intended to indicate that each step is essential to the method or that each step must occur in the order disclosed.

Figure 1:
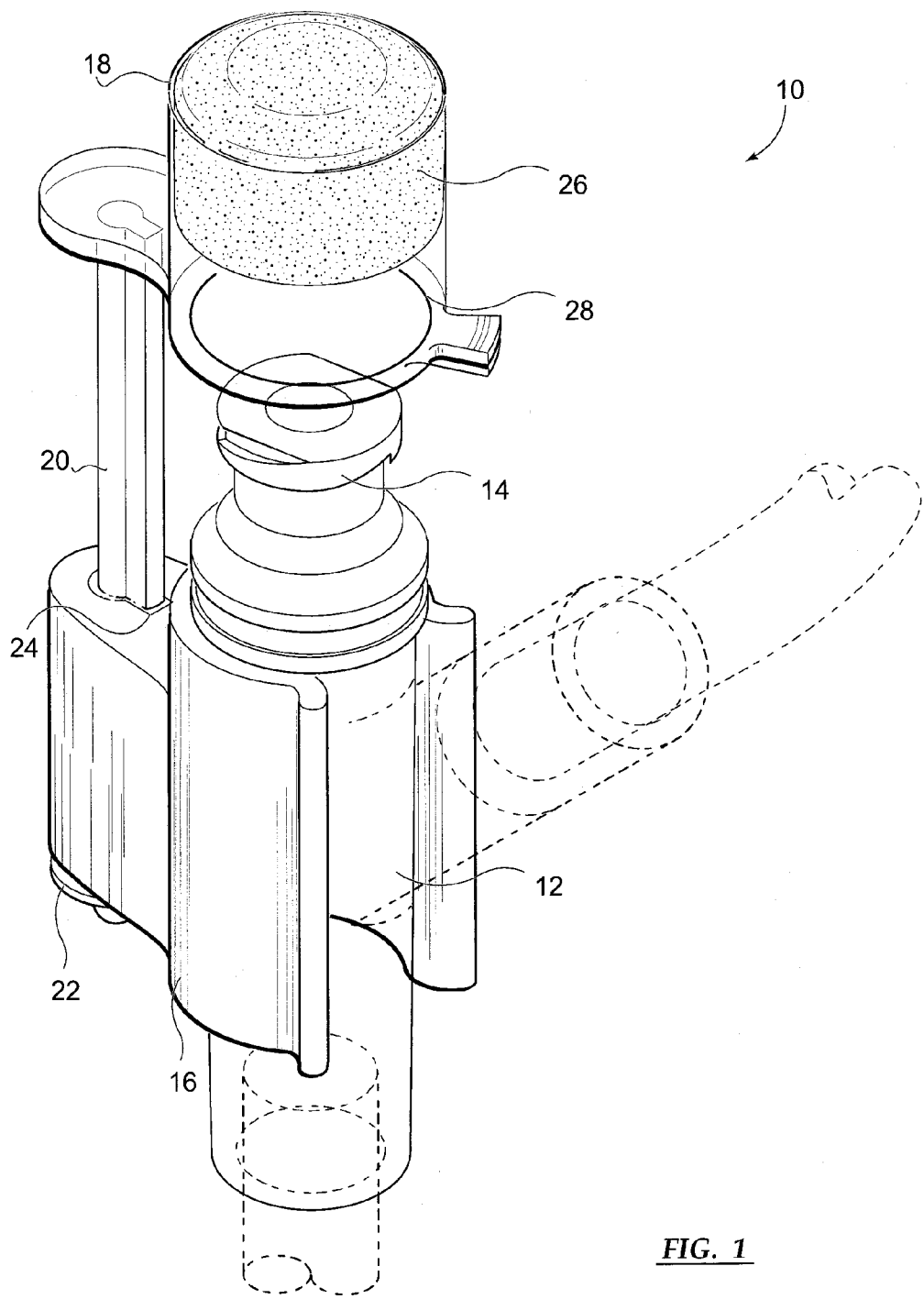
FIG. 1 illustrates one embodiment of the safety device.

A first form of the safety device 10 according to the invention is generally shown in FIG. 1. The safety device 10 is for a medical implement having a body 12 with an inlet end portion 14. The safety device 10 comprises a bracket 16 for mounting on the body 12 of the medical implement; a cap 18 supported by the bracket 16 and sized to fit over and seal the inlet end portion 14 of the medical implement in a safety position wherein the cap 18 covers the inlet end portion 14 of the medical implement. An elongate shaft 20 having a longitudinal axis, the shaft 20 being secured to the cap 18 and being slidably and pivotally supported by the bracket 16 so that the cap 18 can sequentially be raised away from the inlet end portion 14 of the medical implement and be pivoted about the longitudinal axis of the shaft 20 at least 180 degrees away from the inlet end portion 14 and a biasing means 22 biasing the cap 18 to the safety position.

Generally, the inlet end portion 14 is the access port where a practitioner would introduce or withdraw fluids to or from a patient. The medical implement preferably comprises a needleless connector, hub or injection port and its uses are well known in the art. A wide variety of plastics are commonly used to manufacture the external housing and internal components of needleless connectors, although other materials such as silicone and stainless steel are also used. Likewise, these materials can also be used to manufacture the safety device 10. Plastics are lightweight, waterproof, moldable, and typically resistant to chemicals, and can be colorized. The biomaterials used in the manufacturing can include, but are not limited to, the following products: silicone, polyester, polyethylene, polycarbonates, and stainless steel.

Polyethylene is a major synthetic thermoplastic polymer commonly used in IV administration sets. Polycarbonate is easy to work and mold but combines strength, impact and temperature resistance, toughness, and clarity, which are important characteristics. Another significant advantage to polycarbonate is that it can be sterilized by using the ethylene oxide, irradiation, or steam autoclaving methods. In a preferred embodiment, the safety device 10 is free of latex and di(2-ethylhexyl)phthalate.

The bracket 16 is configured to engage the body 12 of the medical implement. Generally, the body 12 of a medical implement is tubular; therefore, in a preferred embodiment the bracket 16 is a horseshoe which securely engages the body 12 of the medical implement. By using the bracket 16, the device 10 can be removably mounted on the body 12.

Figure 2:
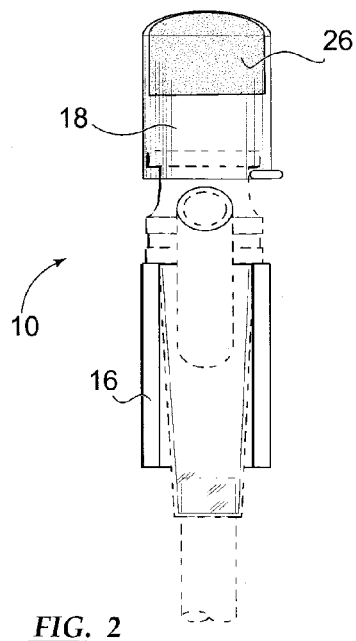
FIG. 2 illustrates a front view of the safety device secured to a medical implement with the cap in a safety position.

As shown in FIG. 2, when the bracket 16 is in a horseshoe configuration it does not add too much width to the medical implement making it uncomfortable for the patient. Additionally, the dimensions and configurations of medical implements can vary, specifically in the body 12. The shape and form of the bracket 16 can be appropriately sized and dimensioned to securely attach to the body 12 depending on the medical implement used. It is contemplated that there are many other methods known in the art to effectively attach the safety device 10 to the medical implement.

Figure 3:
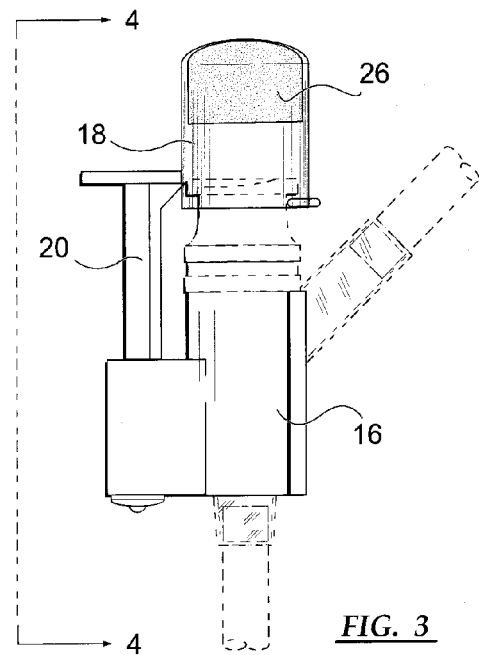
FIG. 3 illustrates a side view of the safety device.
Figure 12A:
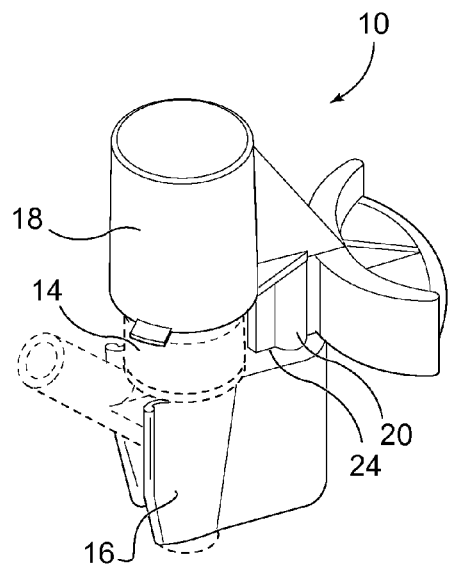
FIGS. 12A-12C illustrate another embodiment of the safety device.
Figure 12B:
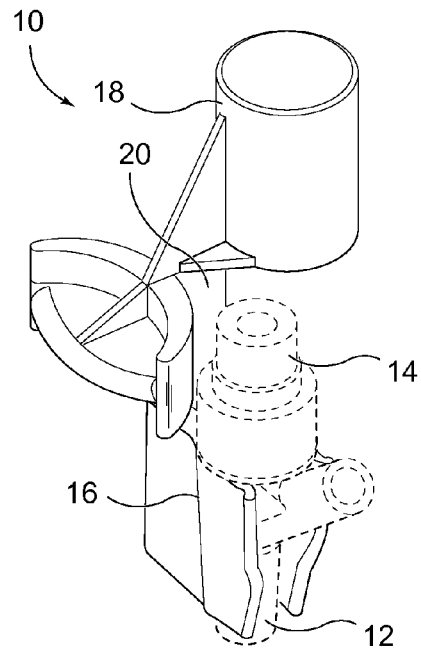
Figure 12C:
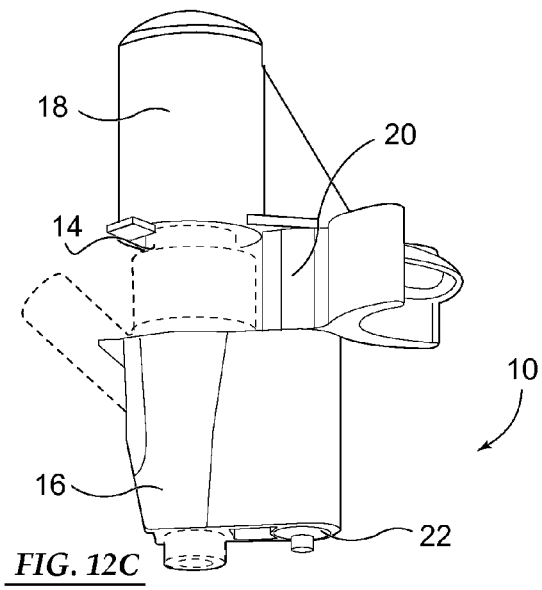

FIG. 3 illustrates another view of the safety device 10 which shows the bracket 16 also functioning to house the shaft 20 and biasing means 22. The elongate shaft 20 having a longitudinal axis is secured to the cap 18 and is slidably and pivotally supported by the bracket 16. The cap 18 can be raised away from the inlet end portion 14 of the medical implement and be pivoted about the longitudinal axis of the shaft 20 away from the inlet end portion 14. In a preferred embodiment, the cap 18 can be pivoted about the longitudinal axis of the shaft 20 at least 1 to 90 degrees away from the inlet end portion 14 of the medical implement. In a most preferred embodiment, the cap 18 can be pivoted about the longitudinal axis of the shaft 20 at least 91 to 180 degrees away from the inlet end portion 14 of the medical implement. The top of the shaft 20 where the cap 18 is attached can be ergonomically modified so that it is suitable for moving the shaft 20 away from the inlet end portion 14. This is best illustrated in FIGS. 12A-12C. For example, the surface can be larger in size to accommodate the finger(s) of the practitioner.

Figure 4:
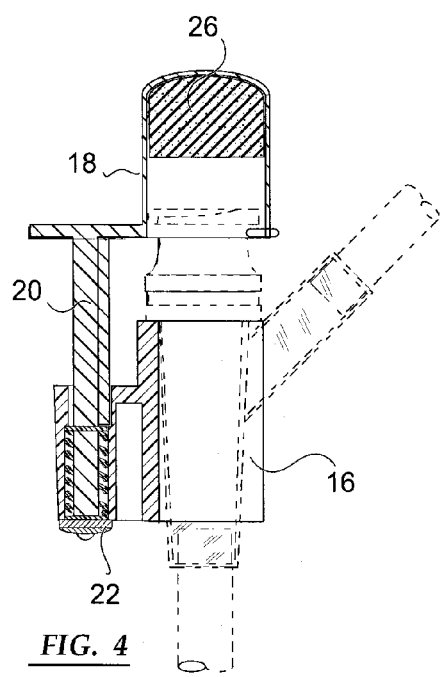
FIG. 4 illustrates a sectional view of the safety device of FIG. 3 taken on line 4-4 in FIG. 3.

As illustrated in FIG. 4 a cross sectional view of the safety device 10, the shaft 20 is mounted to the body 12 in a groove although any other suitable means for rotational displacement can be used. The biasing means as illustrated is a spring 22 although other forms for moving to a desired position can be used. The spring 22 is located at the bottom of the shaft 20 in the interior groove of the bracket 16. The spring 22 also provides height so that the shaft 20 can be lifted, thereby raising the cap 18 vertically above the inlet portion 14. In this embodiment, the safety device 10 requires two sequential movements to dislocate the protective cap from the access port. For example, in the first movement, the cap is raised vertically away from the body 12 of the medical implement and secondly the cap 18 is pivoted or rotated away from the access site. The spring 22 biases the cap 18 back to the safety position by slidably raising the cap 18 away from the inlet end portion 14 of the medical implement. Thus, the spring 22 is the biasing means. When the cap 18 is displaced the tensioning of the spring 22 increases, urging the cap 18 to the rest position.

Figure 5:
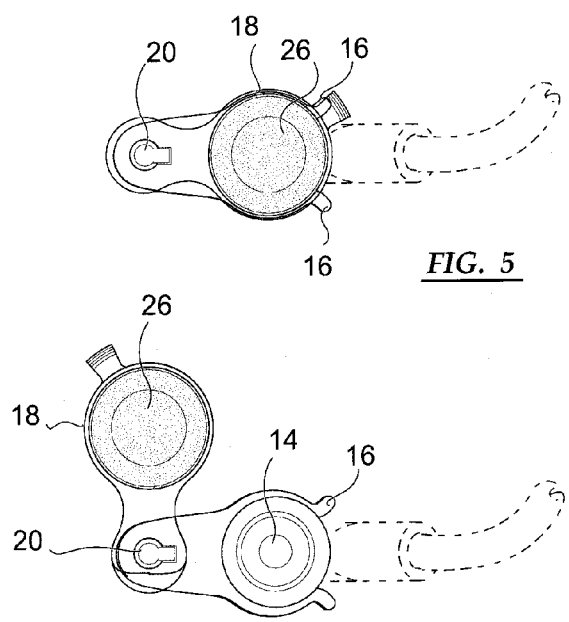
FIG. 5 illustrates a top plan view of the safety device with the cap in the safety position.
Figure 6:
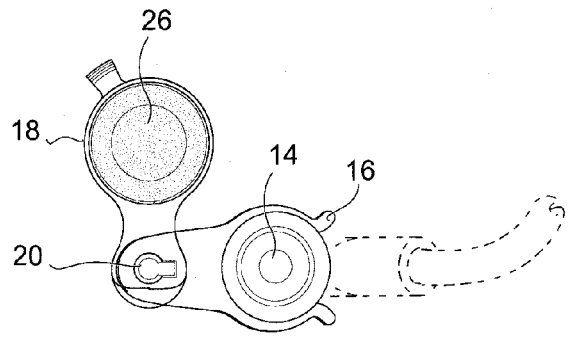
FIG. 6 illustrates a top plan view of the safety device with the cap in a "dislocated" or open position.

The shaft 20 is appropriately mounted to the bracket 16 so that the cap 18 can be displaced from a safety position as shown in FIG. 5, to a position exposing the inlet end portion 14 as shown in FIG. 6. The practitioner is not required to "hold" the cap 18 in the displaced position. In operation, after the injection is made the cap 18 is raised and rotated back toward the inlet end portion 14 "unlocking" the shaft 20 which automatically lowers the cap 18 into the safety position. In this position, a pad 26 housed in the cap 18 bathes the surface of the inlet end portion 14 of the medical implement in disinfecting solution thereby sterilizing the access port.

Figure 7:
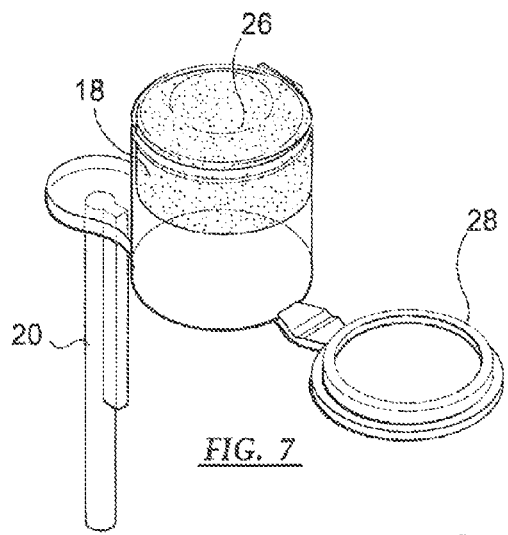
FIG. 7 illustrates a cap and shaft in one embodiment of the safety device.

In FIG. 7 the cap 18 and shaft 20 are shown. In a preferred embodiment, the bottom portion of the elongate shaft 20 is narrower than the upper portion of the shaft 20. This provides a "locking" mechanism 24 so when the cap 18 is raised and displaced the cap 18 is not forcibly asserted toward the inlet end portion 14 or against the practitioner when making an injection. The placement of the locking mechanism 24 will determine how far the cap 18 can be pivoted about the longitudinal axis of the shaft 20 away from the inlet end portion 14 of the medical implement.

The cap 18 of the safety device 10 is supported by the bracket 16 and sized to fit over and seal the inlet end portion 14 of the medical implement in a safety position wherein the cap 18 covers the medical implement. The cap 18 houses the pad 26, sponge, or any other material having disinfecting or anti-microbial properties. Preferably, the pad 26 is presoaked with a disinfectant. Common disinfectants that can be used are alcohol, isopropyl alcohol, chlorohexidine and combinations thereof. When the cap 18 is in safety position the pad 26 is in contact with the inlet portion 14 of the medical implement keeping the access site safe and clean. Optionally, the bottom portion of the cap 18 has a rim 28. The rim 28 creates a tighter fit around the inlet end portion 14 of the medical implement preventing contamination and the escape of the disinfecting fluid from evaporation. The rim 28 can also function to hold the pad 26 in place when the cap is displaced from the safety position.

The effectiveness of the disinfectant can decrease with time. Therefore, it is desirable to have a visible indicator to signal when a "new" safety device 10 is required. For example, the cap 18 can be partially or completely clear or opaque so the practitioner can see through the cap 18 to determine when the disinfectant solution is low in volume. The disinfectant can be dyed a color and as the disinfectant disappears, the color will become less vibrant indicating a need to change the safety device 10. When changing the safety device 10 the practitioner simply removes the bracket 16 from the body 12 of the medical implement and secures a new safety device 10 to the body 12.

Optionally, the bracket 16 of the safety device 10 can be molded as one piece with the body of the medical implement. In this embodiment, the disinfectant will likely wear off before the need arises for a new medical implement. For this reason, it is contemplated that the safety device can be configured so that a new shaft 20 with cap 18 attached can be inserted into the safety device 10. For example once the disinfectant is no longer effective the practitioner can remove the shaft 20 from the safety device 10 and insert or attach a new shaft 20 with cap 18 attached.

Figure 8:
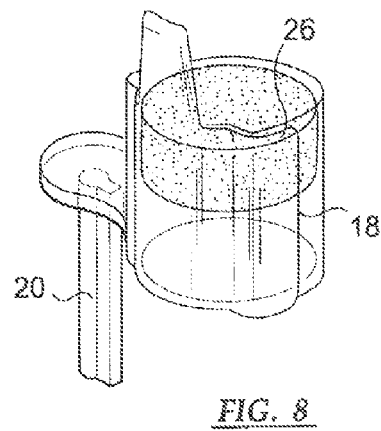
FIG. 8 illustrates another embodiment of a cap.
Figure 9:
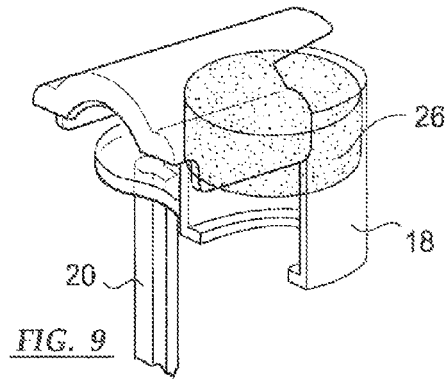
FIG. 9 illustrates a cap in FIG. 8 in an open position.
Figure 10:
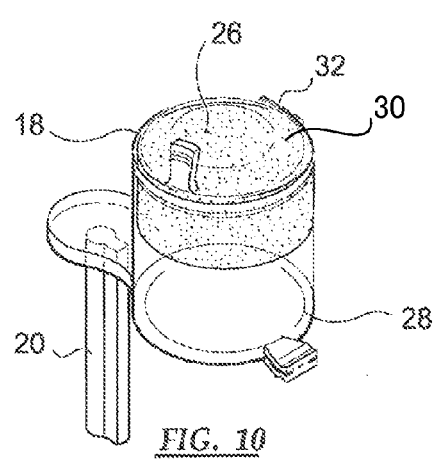
FIG. 10 illustrates another embodiment of a cap.
Figure 11:
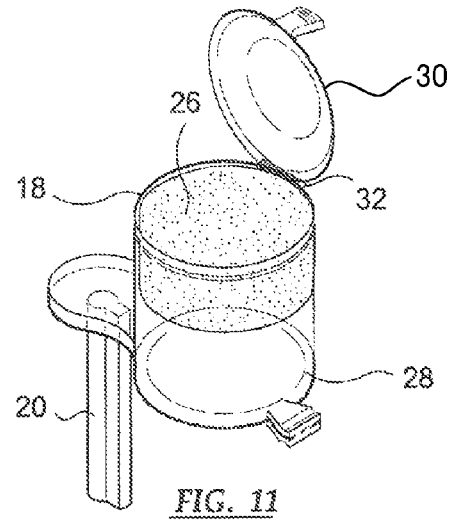
FIG. 11 illustrates the cap in FIG. 10 in an open position.

Alternatively, the cap 18 can have a hinged door 30 so that the pad 26 can be replaced. In FIGS. 8 and 9, the hinged door 30 is located on the side of the cap 18 or in another alternative as seen in FIGS. 10 and 11, the hinged door 30 when positioned on the top of the cap 18 will function as a lid. The hinged door is connected to the cap with a hinge 32 which is used to displace the hinged door from the cap 18. The hinged door 30 can be opened so that the practitioner can remove the pad 26 and insert a new pad 26. Again, the rim 28 on the bottom portion of the cap 18 will function to hold the pad 26 in place. Optionally, the pad 26 can have an adhesive on the non-disinfecting end. The adhesive can attach the pad 26 to the interior cavity of the cap 18. After the disinfectant is no longer effective, the practitioner can open the cap 18, remove the used pad 26 and insert a new pad 26 into the cap 18 without having to replace the entire safety device 10.

FIGS. 12A through 12C are illustrations of another embodiment of the safety device 10. In use, a practitioner can attach the safety device 10 to a medical implement. The cap 18 is securely placed over the inlet end portion 14 of the medical implement. When accessing the medical implement the practitioner will raise the shaft 20 vertically above the inlet end portion 14 high enough so the shaft 20 is raised above the locking mechanism 24. Once past the locking mechanism 24 the practitioner rotates the cap 18 in either direction away from the inlet end portion 14 of the medical implement. The practitioner can make the injection, unlock the cap 18 and rotate the cap 18 back toward the inlet end portion 14. When the shaft 20 is aligned with the locking mechanism 24 the cap 18 will automatically be lower covering the inlet end portion 14 of the medical implement.

Materials and Methods

Methods and materials are described herein. However, methods and materials similar or equivalent to those described herein can be also used to obtain variations of the present invention. The materials, methods, and examples are illustrative only and not intended to be limiting.

INCORPORATION BY REFERENCE

Throughout this application, various publications, patents, and/or patent applications are referenced in order to more fully describe the state of the art to which this invention pertains. The disclosures of these publications, patents, and/or patent applications are herein incorporated by reference in their entireties, and for the subject matter for which they are specifically referenced in the same or a prior sentence, to the same extent as if each independent publication, patent, and/or patent application was specifically and individually indicated to be incorporated by reference.

Other Embodiments

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A safety device for use with a medical implement having a body with an inlet end portion, the safety device comprising:
   a) a bracket for mounting on the body of the medical implement;
   b) a cap supported by the bracket and sized to fit over and seal the inlet end portion of the medical implement in a safety position;
   c) an elongate shaft having a longitudinal axis, the shaft being secured to the cap and being slidably and pivotally supported by the bracket so that the cap can be raised away from the inlet end portion of the medical implement and be pivoted about the longitudinal axis of the shaft away from the inlet end portion; and
   d) biasing means for biasing the cap to the safety position.

2. The safety device of claim 1, further comprising a medical implement having a body where the bracket is molded as one piece with the body of the medical implement.

3. The safety device of claim 1, further comprising a releasable lock, where the releasable lock temporarily secures the cap away from the inlet end portion of the medical implement.

4. The safety device of claim 1, where the cap has an interior space defining an area for an antimicrobial agent.

5. The safety device of claim 4, where the interior space comprises an antimicrobial agent such that the antimicrobial agent is configured to contact the inlet end portion of the medical implement in the safety position.

6. The safety device of claim 5, where the antimicrobial agent is selected from the group comprising, alcohol, isopropyl alcohol, chlorohexidine and combinations thereof.

7. The safety device of claim 4, where the cap further comprises a rim, where the rim supports the antimicrobial agent.

8. The safety device of claim 5, where the cap further comprises a hinged door where the hinged door can be opened so that the antimicrobial agent can be removed or inserted.

9. The safety device of claim 5, further comprising an indicator which visually signals a change in the antimicrobial agent.

* * * * *